US00PP33995P3

(12) United States Plant Patent
Takano

(10) Patent No.: US PP33,995 P3
(45) Date of Patent: Mar. 8, 2022

(54) APPLE TREE NAMED 'TAKANO 6'

(50) Latin Name: *Malus domestica*
Varietal Denomination: Takano 6

(71) Applicant: Takao Takano, Oshu (JP)

(72) Inventor: Takao Takano, Oshu (JP)

( * ) Notice: Subject to any disclaimer, the term of this patent is extended or adjusted under 35 U.S.C. 154(b) by 0 days.

(21) Appl. No.: 16/873,248

(22) Filed: Mar. 4, 2020

(65) Prior Publication Data

US 2020/0288613 P1 Sep. 10, 2020

Related U.S. Application Data

(60) Provisional application No. 62/815,525, filed on Mar. 8, 2019.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

(56) References Cited

PUBLICATIONS

UPOV hit on apple tree named, 'Takano-6Go', JP PBR 27547, published Mar. 21, 2018.*

*Malus pumila* Apple, The Jepson Herbarium, University of California Berkeley, downloaded Jun. 17, 2021 from https://ucjeps.berkeley.edu/eflora/eflora_display.php?tid=32587.*

* cited by examiner

*Primary Examiner* — Anne Marie Grunberg
(74) *Attorney, Agent, or Firm* — Leydig, Voit & Mayer, Ltd.

(57) ABSTRACT

A new and distinct variety of apple tree is described, the variety resulting from controlled cross pollination between (Fuji x Shinano Gold). This variety can be characterized by its full red coloration and crisp texture. The new variety has been named 'Takano 6'.

9 Drawing Sheets

Genus and species plant claimed: *Malus domestica.*
Variety denomination: 'Takano 6'.

BACKGROUND OF THE INVENTION

The new variety of apple tree, *Malus domestica*, resulted from controlled cross pollination between (Fuji x Shinano Gold). The new variety was determined to be distinct from the parent varieties.

The new variety is a product of a planned breeding program conducted during a period from May 2006 to September 2017 in Iwate, Japan, in which the *Malus* Mill, variety 'Shinano Gold' (female parent; Japanese Variety Registration No. 7328, registered Aug. 11, 1999) was crossed with the *Malus pumila* variety 'Fuji' (male parent). The objective of the breeding program was to create new apple varieties that produce fruits having long common storage duration and firm flesh, different from those of the parents and known similar varieties. Asexual reproduction was performed by grafting in Iwate, Japan.

The new and distinct variety 'Takano 6' has a high sweetness (about 16 (Brix %)) and medium acidity (about 0.41 g/100 ml) of the fruit, higher firmness of the flesh (about 14.5 lbs.), and late harvest time (late October, early November in Japan). The new variety, as described below, is distinct from the known variety 'Shinano Gold' (female parent) that was produced by crossing the *Malus* Mill variety 'Golden Delicious', a classic American apple variety, with the known variety 'Senshu' (Japanese Variety Registration No. 42, registered Mar. 31, 1980). The new variety is also distinct from the known variety 'Fuji' (male parent) that was a produced in Japan from crossing *Malus* Mill variety Red Delicious with *Malus* Mill variety Ralls Janet (also known as Ralls Genet and Rawls Jennet).

SUMMARY OF THE INVENTION

This variety can be characterized by its full red coloration (RHS Red-Purple Group 63A to 63B) and firm texture (about 14.5 lbs). The variety is also different in that the harvest time is one week earlier (late October, early November) and the fruit has a higher acidity (about 0.41 g/100 ml titratable acid) than Fuji (about 0.35 g/100 ml titratable acid). The new variety has been named 'Takano 6'.

BRIEF DESCRIPTION OF THE DRAWINGS

The accompanying photographs show typical specimens of the tree, foliage and fruit of the new variety as depicted in colors as nearly true as is reasonably possible to make the same in a color illustration of this character.

DETAILED DESCRIPTION

Figure 1:
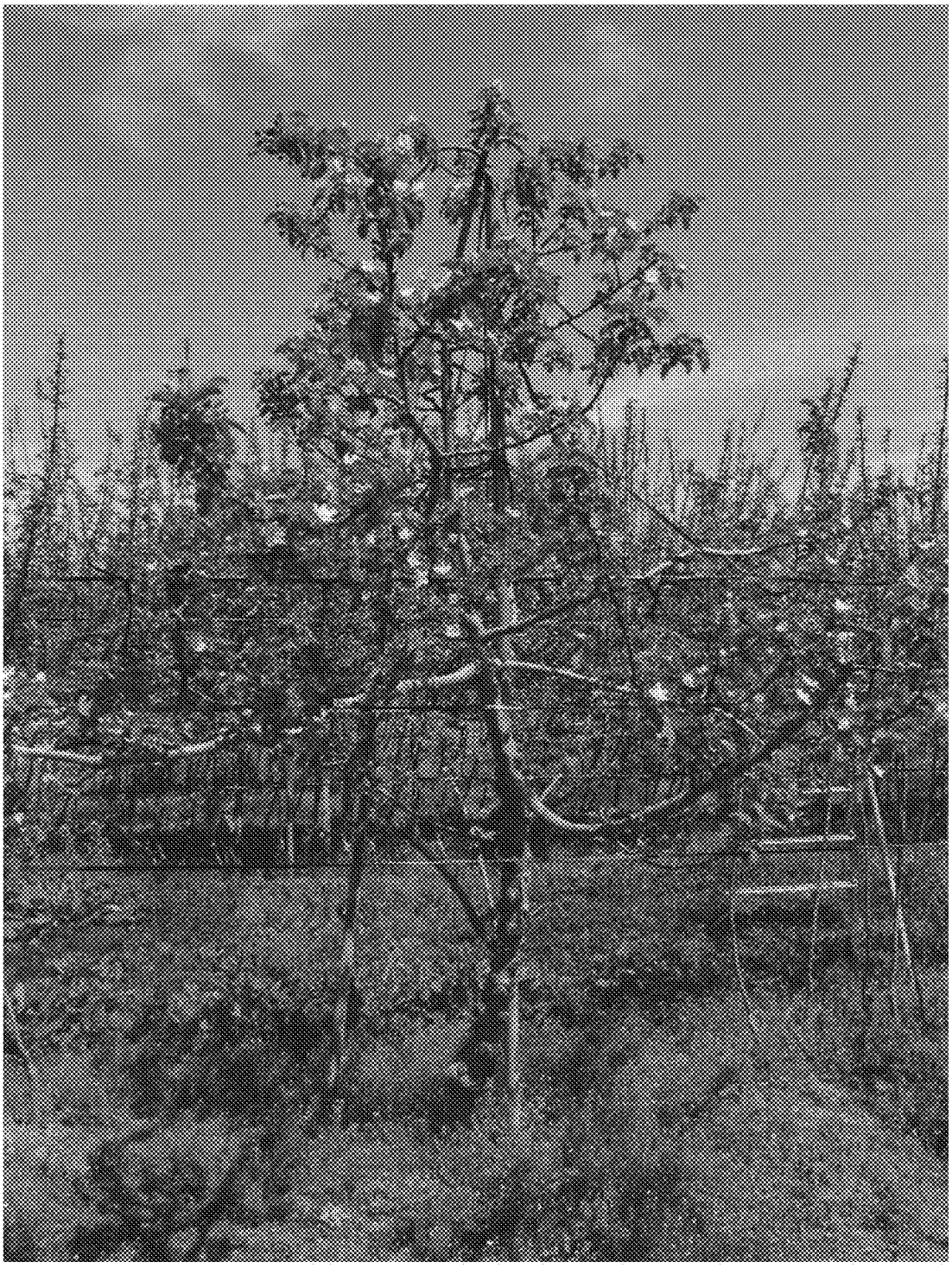
FIG. 1 shows the tree in flower.
Figure 2:
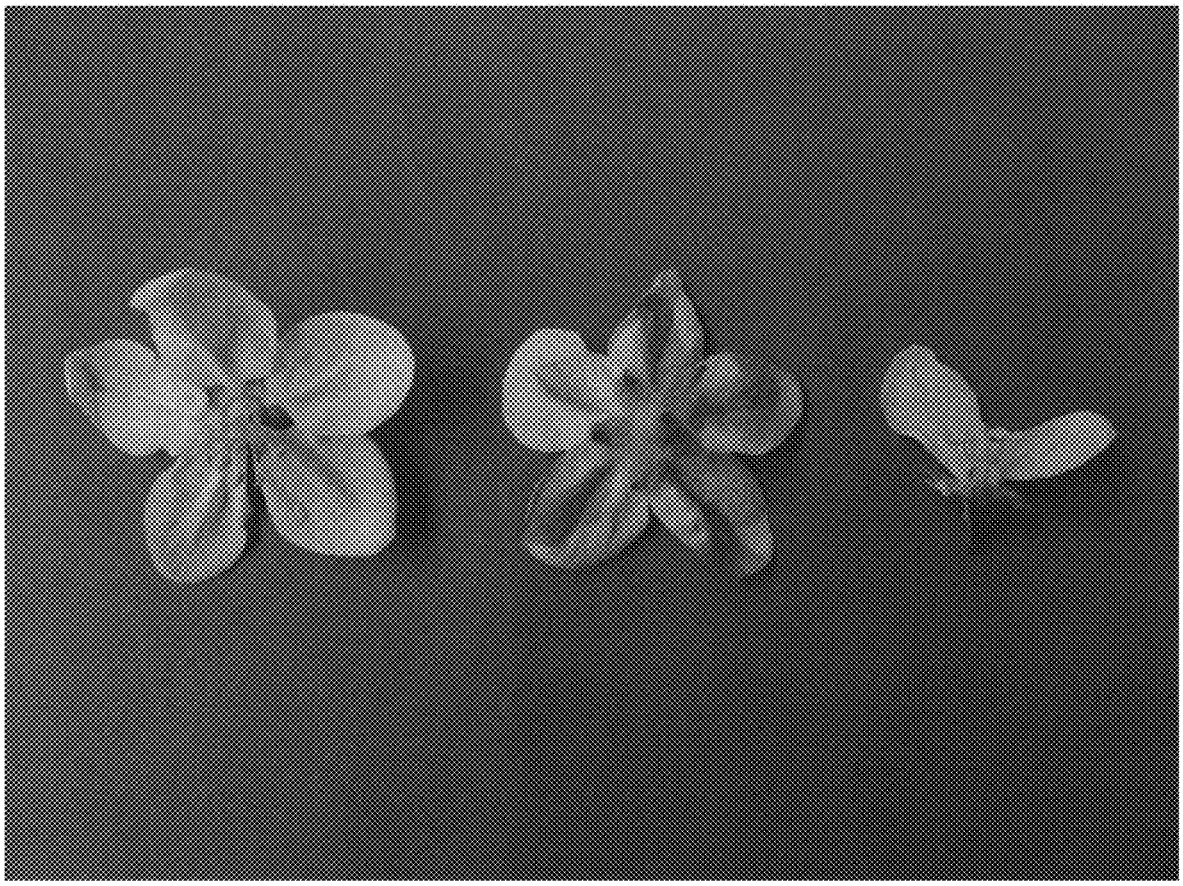
FIG. 2 shows flowers from above, below and in section.
Figure 3:
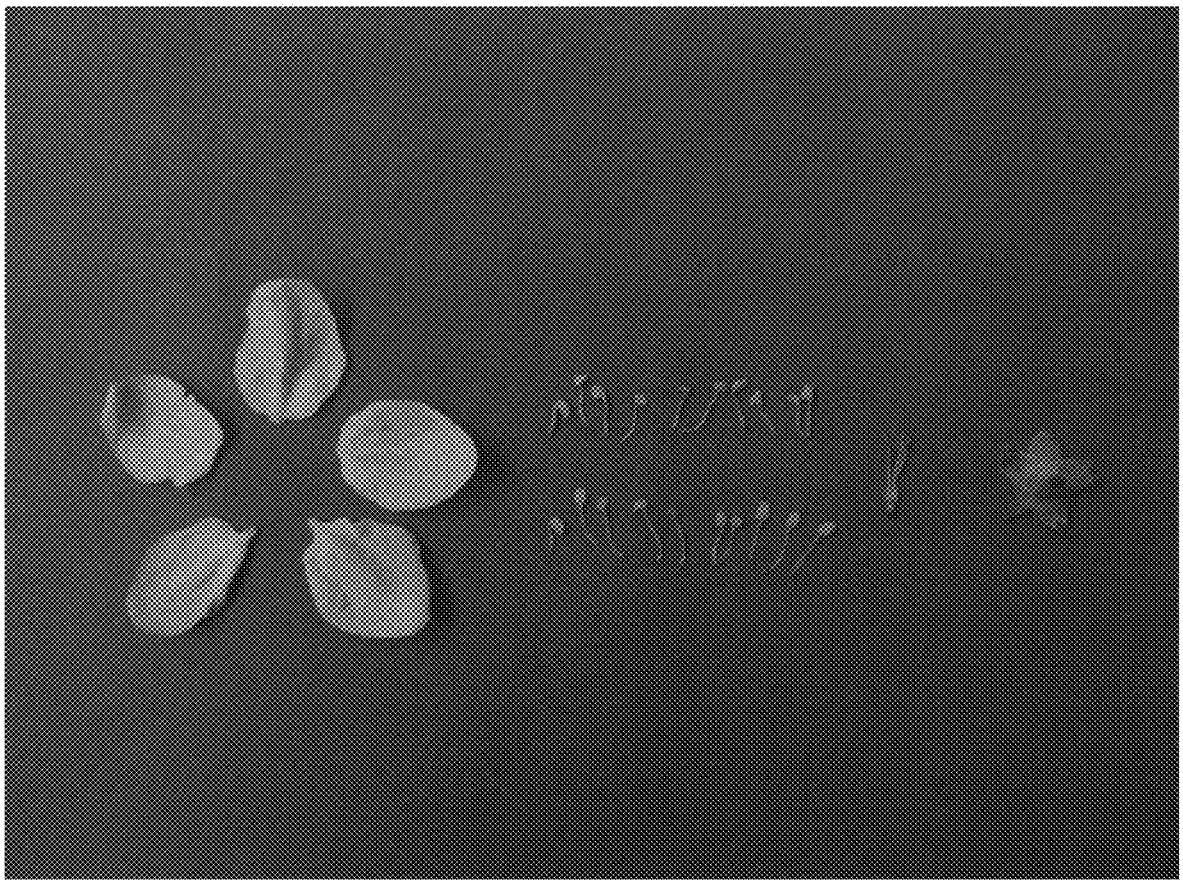
FIG. 3 shows detached flower parts.
Figure 4:
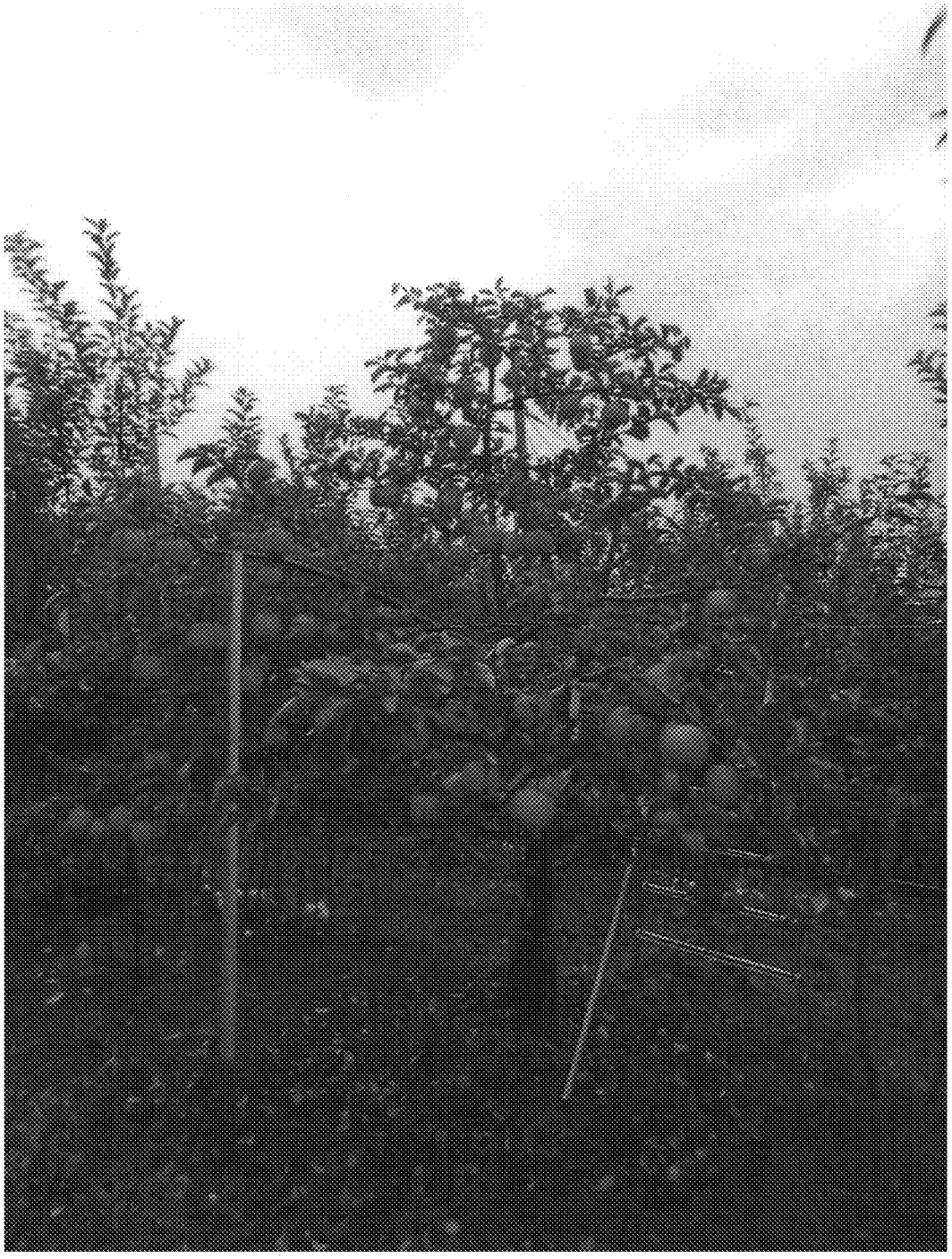
FIG. 4 shows the tree in fruit.
Figure 5:
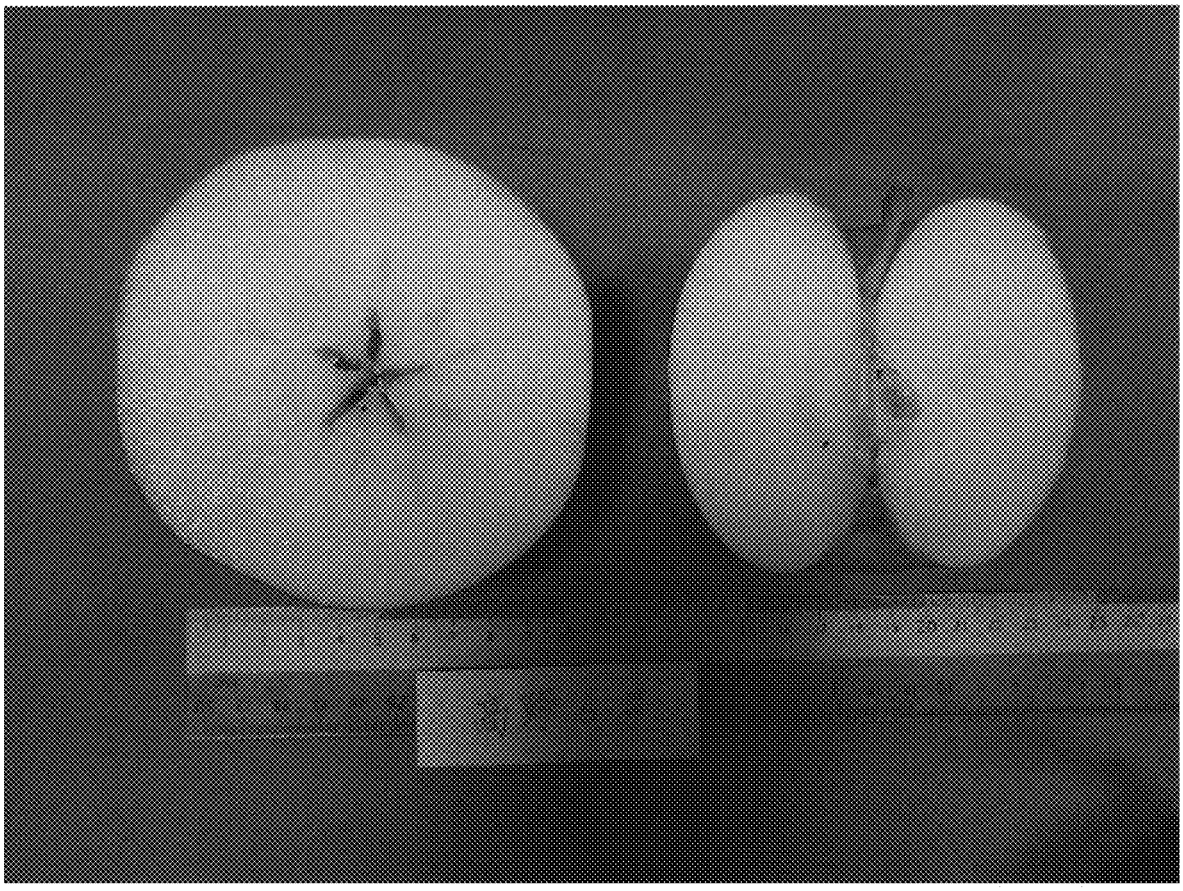
FIG. 5 shows fruit in transverse and vertical section.
Figure 6:
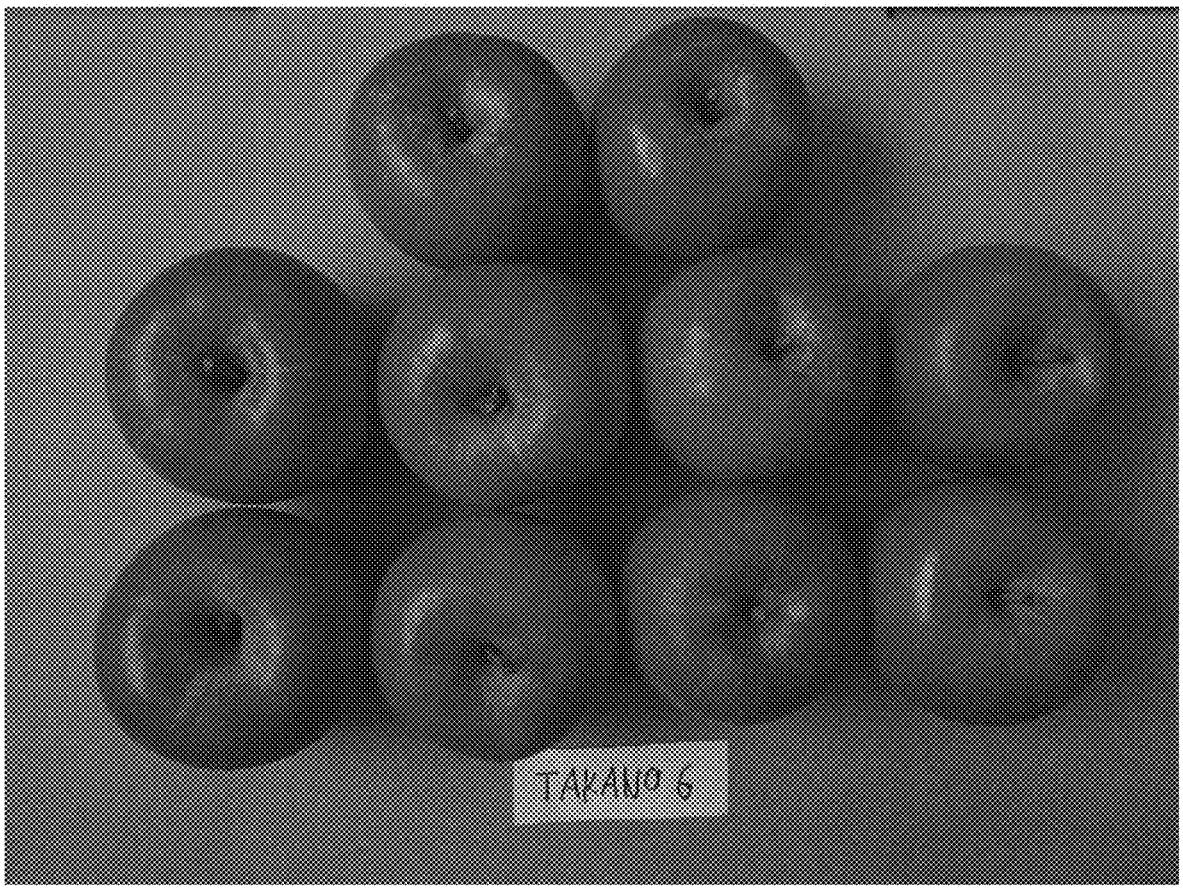
FIG. 6 shows several fruit from above.
Figure 7:
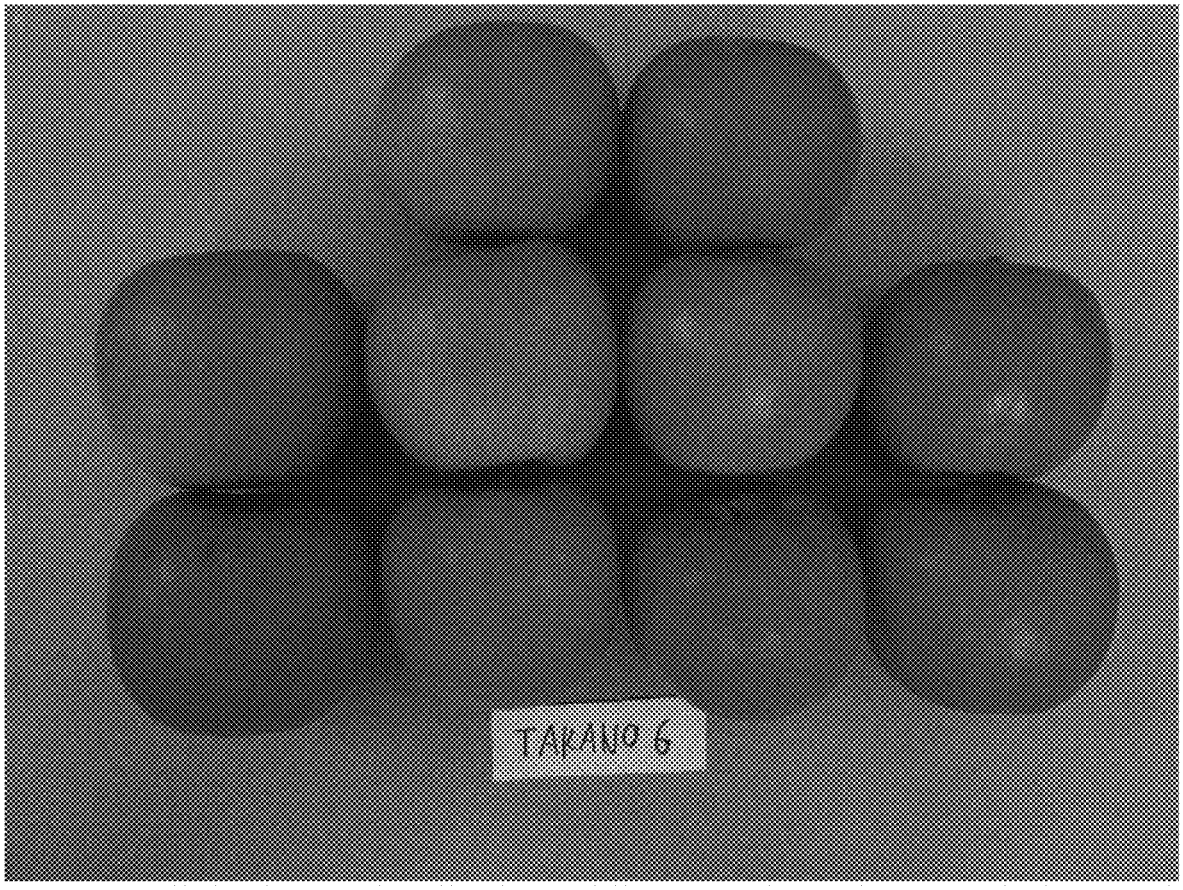
FIG. 7 shows several fruit from a side view.
Figure 8:
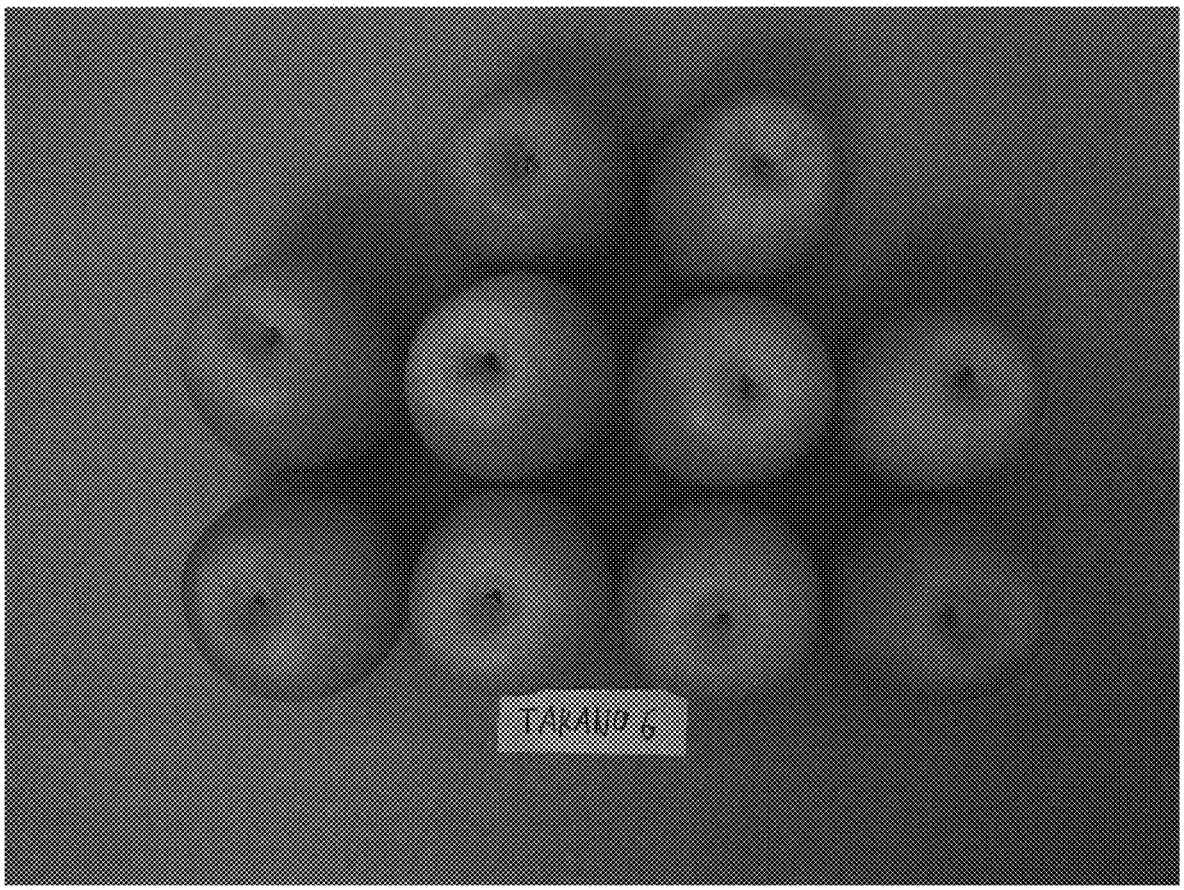
FIG. 8 shows several fruit from below.
Figure 9:
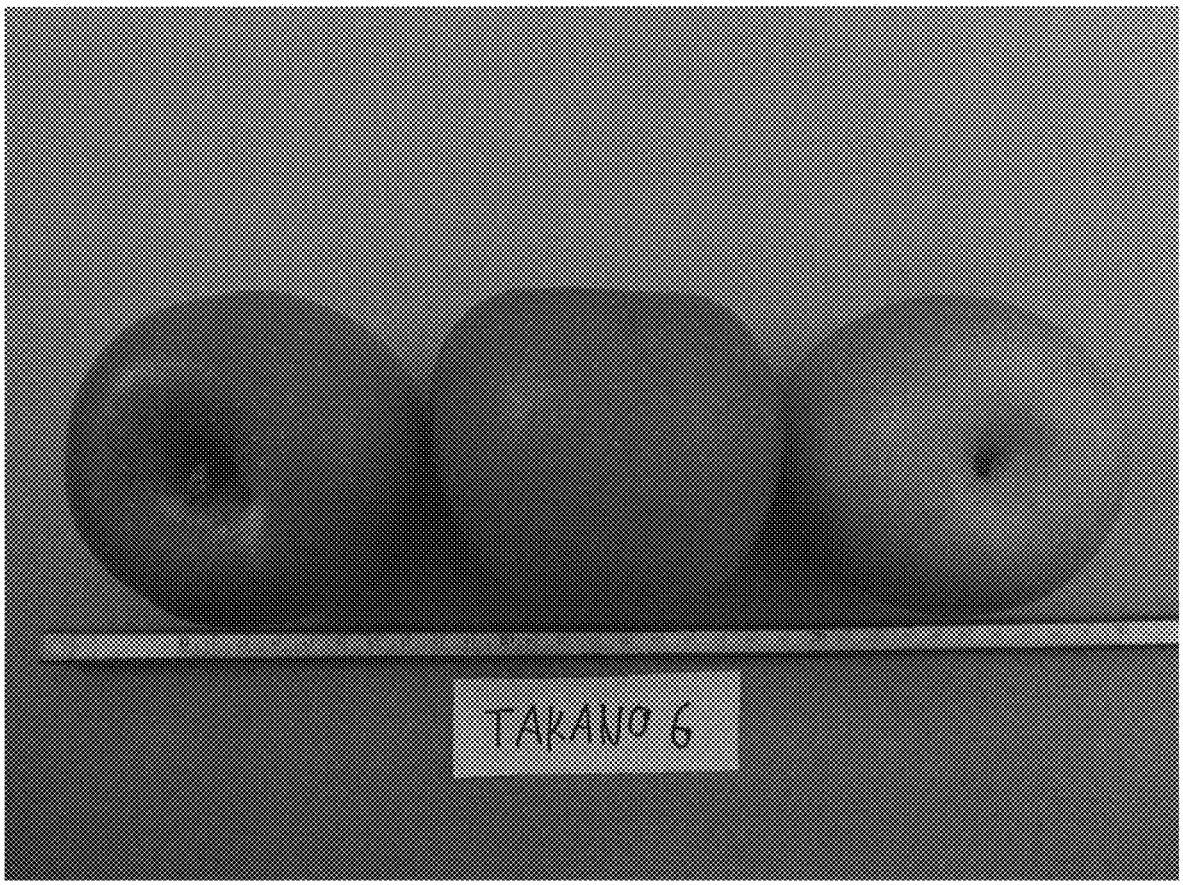
FIG. 9 shows fruit from above and in side view.

The following detailed botanical description of 'Takano 6' apple tree is based on a survey (or observations) made during the period between March 2018 and November 2019 at Iwate, Japan as well as additional observations made in 2021 on trees planted in Loire Valley, France. All colors are described according to The Royal Horticultural Society (R.H.S.) Colour Chart, 6th edition 2019 reprint. It should be understood that the characteristics described will vary somewhat depending upon cultural practices and climate conditions and will also vary depending upon location and season. Quantified measurements are generally expressed as an average of measurements taken from individual trees of 'Takano 6' unless otherwise noted; however, the measurements of any individual plant or any group of plants of 'Takano 6' may vary from the stated average. The majority of trees in these observations were 8 years old at the end of the observation period.

Information on the breeding scheme and propagation of the variety:

*Breeding*.—Produced by controlled pollination.
*Parents*.—(Fuji x Shinano Gold).
*Method of propagating the variety through vegetative propagation*.—Typically by grafting on JM1 (Japanese Variety Registration No. 7443, registered Sep. 21, 1999) root-stock; and the time of grafting is a period of mid to late March at Iwate, Japan.

Characteristics of the variety:

*Tree type*.—Ramified.
*Tree habit*.—Spreading.
*Spread of mature tree*.—1.7 m after pruning.
*Height*.—2.35 m after pruning.
*Vigor*.—Medium.
*Trunk diameter*.—35.5 mm.
*Bearing*.—Both shoots and spurs.
*Bark texture*.—Rough.
*Bark color*.—RHS brown group N200D+reflection RHS greyed-orange group 177A.
*Lenticel length*.—2 mm.
*Lenticel width*.—1.1 mm.
*Lenticel shape*.—Elliptic slightly elongated.
*Lenticel density per cm*$^2$.—Many.
*Lenticel color*.—RHS greyed-green group 197C.

Branches (fruiting branches located at around 1 m above the graft union):

*Length*.—1.1 M.
*Diameter*.—21.8 mm. Crotch angle 80°.
*Color*.—RHS brown group N200D+reflection RHS greyed-orange group 177A.
*Branch lenticel length*.—1.8 mm.
*Branch lenticel width*.—0.9 mm.
*Branch lenticel shape*.—Elliptic, slightly elongated.
*Branch lenticel density per cm*$^2$.—Medium to many.
*Branch lenticel color*.—RHS greyed-green group 197C.

One year old shoots:

*Length*.—20.8 cm.
*Diameter*.—4.1 mm.
*Pubescence*.—Medium.
*Color*.—RHS greyed-orange group 165A.
*Internode length*.—2.7 mm.
*Shoot lenticel length*.—1.2 mm.
*Shoot lenticel width*.—0.8 mm.
*Shoot lenticel shape*.—Elliptic slightly elongated.
*Shoot lenticel density per cm*$^2$.—Medium.
*Shoot lenticel color*.—RHS orange-white group 159C.

Fruit:

*Fruit general shape*.—Globose~obloid.
*Diameter*.—78 mm. Height: 66 mm. Weight 212 g.
*Ratio of height to width*.—Large (0.85).
*Position of maximum diameter*.—Middle.
*Ribbing*.—Absent or weak.
*Crowning at calyx end*.—Absent or weak.
*Seize of eye*.—Small.
*Aperture of eye*.—Open to close.
*Depth of eye basin*.—8.4 mm.
*Width of eye basin*.—31.3 mm.
*Sepal length*.—4.4 mm.
*Bloom of skin*.—Absent or weak.
*Greasiness of skin*.—Absent or weak.
*Background of color of skin*.—Yellow.
*Over color of skin*.—RHS Orange-Red Group N34A.
*Intensity of over color*.—Weak.
*Pattern of over color*.—Solid flush with weakly defined stripes.
*Relative area of fruit over color*.—Large (similar to Jonagold).
*Amount of russet around stalk cavity*.—Medium.
*Amount of russet on cheeks*.—Absent or weak.
*Area of russet around eye basin*.—Absent or small.
*Length of stalk*.—Medium (2.1 cm).
*Thickness of stalk*.—Medium (1.9 mm).
*Depth of stalk cavity*.—Medium (1.9 mm).
*Width of stalk cavity*.—Medium (4.4 cm).
*Stalk color*.—RHS greyed-orange group 165A.
*Firmness of flesh*.—Medium.
*Flesh texture*.—Medium to good.
*Aroma*.—Good and medium intensity.
*Juiciness*.—Medium to very juicy.
*Brix*.—15.
*Flesh color*.—RHS yellow group 4D.

Seeds:

*Quantity per fruit*.—4.3.
*Shape*.—Ovate.
*Color*.—RHS greyed-orange group 166A.
*Length*.—9.4 mm.
*Width*.—4.7 mm.

Flower buds:

*Stage described*.—53 BBCH.
*Quantity per spur*.—5.
*Bud shape*.—Elliptic.
*Apex shape*.—Round.
*Length*.—9 mm.
*Diameter*.—6 mm.
*Color*.—RHS greyed-purple group N186C.

Flowers:

*Inflorescence type*.—Umbel.
*Diameter of fully open flower*.—4.3 cm.
*Depth of fully open flower*.—1.1 cm.
*Relative position of petal margin* (*overlapping, touching, or free*).—Touching.
*Number per cluster*.—5.5.
*Time of beginning of flowering* (10% *open flowers*).—Medium (same as Fuji), i.e. in Japan, the last week of April.
*Date of first bloom in France*.—Mid-late April (two days after Gala).
*Date of full bloom in France*.—Late-April (two days after Gala).

Petals:

*Number per flower*.—5.
*Petal shape*.—Slightly elongated, elliptic.
*Length*.—19.7 mm.
*Width*.—14.1 mm.
*Apex shape*.—Rounded.

*Base shape*.—Broad wedge-shaped, straight.
*Margin*.—Entire.
*Color of upper surface*.—RHS white group NN155D.
*Color of lower surface*.—RHS red-purple group 70B.
*Color of venation*.—RHS red-purple group 70A.
*Petal vein prominence*.—Medium.
*Pistil length*.—11 mm.
*Pistil color*.—RHS yellow-green group N144D.
*Stigma diameter*.—0.6 mm.
*Stigma color*.—RHS greyed-orange group 167A.
*Position of stigma relative to anther*.—Same level.
*Style length*.—7.7 mm.
*Style color*.—RHS yellow-green group N144D.
*Ovary length*.—2.9 mm.
*Ovary color*.—RHS white group NN155D.
*Stamens quantity*.—19.3 mm.
*Stamen length*.—8.6 mm.
*Anther color*.—RHS yellow group 8C.
*Presence/amount of pollen*.—Scarce to medium.
*Pollen color*.—RHS yellow group 10B.
*Pedicel length*.—20 mm.
*Pedicel diameter*.—1.7 mm.
*Pedicel color*.—RHS greyed-orange group 166A+RHS yellow-green group 144A.
*Sepal quantity*.—5.
*Sepal color*.—RHS yellow-green group 144B.
*Sepal shape*.—Slightly elongated triangular.
*Apex shape*.—Acute.
*Margin*.—Entire.
*Leaf length*.—Medium (10.7 cm).
*Leaf width*.—Medium (6.5 cm).
*Leaf length/width ratio*.—Medium (1.65).
*Leaf attitude in relation to shoot*.—Outwards.
*Petiole length*.—Medium (2.6 cm).
*Harvest date*.—Late October, early November (one week earlier than Fuji).
*Time of eating maturity*.—Late (one week earlier than Fuji in Iwate, Japan), i.e. late October, the first week of November.

Other characteristics of the variety:

| Characteristic | Takano 6 |
|---|---|
| Duration of storage | variety has average storage potential |
| the growth pattern of one year old shoots | straight |
| description of any leaf lobes | broad ovate leaf with broad wedge-shaped convex base and narrow short acuminate apex |
| leaf blade profile in cross-section | concave |
| undulations of leaf blade margins | 1 to 3 large undulation per leaf blade ride |
| leaf blade incisions of the margin for both the upper half and lower half of the blade | serrate |
| length of leaf blade tip | 0.5 cm |
| leaf blade depth of margin incisions | 0.2 cm |
| leaf blade pubescence on lower side | lanate, weak |
| glossiness of the upper side of the leaf blade | medium |
| extent of petiole anthocyanin coloration from the base | 0.5 cm from base |
| size of the vegetative bud on one year old shoot | 0.5 × 0.4 cm |
| size of vegetative bud support on the one-year-old shoot | 0.6 × 0.2 cm |

-continued

| Characteristic | Takano 6 |
|---|---|
| shape of the vegetative bud apex | acute |
| description of pubescence on the lower leaf blade | lanate, weak |
| stipule size | 0.5 × 0.2 cm |
| regularity of bearing | regular |
| amount of fruit set | 60 fruits per tree on average on 2 m high on 4 year old tree |
| size of the eye | 0.9 cm |
| fruit calyx size | 3.5 cm |
| color of new shoots | N199B |
| color of internodes | N199B |
| color of lenticles on the fruit | 155A |
| color of expanding leaf blade | 144A |
| color of upper leaf blade | 139A |
| color of lower leaf blade | 147C |
| color of autumn leaf blade coloration | 153A |
| color of leaf venation | 145C |
| color of leaf lobes | 139A |
| color of vegetative buds | 200C |
| color of petiole | 145C with N14C reflects |
| color of anthocyanin colorations petiole | 183C |
| color of anthocyanin colorations developing fruit | 165B |
| color of anthocyanin colorations mature fruit | 34C |

Description of similar varieties. The variety 'Shinano Gold', the female parent, has skin color that is yellow (RHS Yellow Group approximately 6C) when harvested, the sweetness of flesh is high (about 15.3 Brix %), the acidity of flesh is medium (about 0.45 g/100 ml), the firmness or food texture (i.e., mouthfeel) of flesh is firm (about 15.5 lbs.), and the time of harvest is late, specifically late October in Iwate, Japan. In contrast, the present variety is a large red colored apple (red over color), slightly higher sweetness (16 Brix %), slightly lower acidity (0.41 g/100 ml), and a firmness of 14.5 lbs.

The variety 'Fuji', the male parent, has skin color that is red when harvested, the sweetness of the flesh is high (about 16 Brix %), the acidity of the flesh is low (about 0.35 g/100 ml), the firmness of the flesh is medium (about 13.5 lbs), and the time of harvest is late, specifically November in Iwate Japan. In contrast, the present variety matures a week earlier than Fuji (late October, early November), has higher flesh firmness (14.5 lbs), and more balanced acidity (0.41 g/100 ml).

The variety 'Aztec'™ was discovered in New Zealand and is a mutation (sport) of the variety 'Fuji'. In addition to the characteristics of 'Fuji' noted above, 'Aztec' has very high "over color" of the fruit.

Additional detailed characteristics are shown in the table below, where the new variety was grown and compared to the Fuji sport, "Aztec", below. Unless shown in millimeters, the description and numbers are provided using the UPOV Test Guidelines for apple varieties (as described in UPOV Document TG14/9).

| Characteristics | State for Takano 6 | Aztec (a Fuji Sport) |
|---|---|---|
| One-year-old shoot thickness | medium (5.1 mm) | medium 5 |
| One-year-old shoot: length of internode | short (3.3 cm) | medium 5 |

-continued

| Characteristics | State for Takano 6 | Aztec (a Fuji Sport) |
|---|---|---|
| One-year old shoot: color on sunny side | medium brown RHS Brown Group 200C | medium 5 |
| One-year-old shoot: pubescence (on distal half of shoot | medium 5 | medium 5 |
| One-year-old shoot: number of lenticels | many 5 | medium 5 |
| Leaf blade: attitude in relation to shoot | outwards 2 | outwards 2 |
| Leaf blade: length | medium 5 (10.7 cm) | medium 5 |
| Leaf blade: width | medium 5 (6.5 cm) | medium 5 |
| Leaf blade: ratio length/width | medium 5 (1.65) | medium 5 |
| Leaf blade: intensity of green color | medium 5 | medium 5 |
| Petiole: length | medium 5 (2.6 cm) | medium 5 |
| Petiole: extent of anthocyanin coloration from base | large 7 | |
| Flower: predominant color at balloon stage | light pink 3, RHS Red-Purple Group 63A to 63B | |
| Flower: diameter with petals pressed into horizontal position | medium 5 (4.0 cm) | |
| Flower: arrangement of petals | intermediate, 2 petals joined | intermediate, 2 petals joined |
| Flower: position of stigmas relative to anthers | same level 2 | |
| Young fruit: extent of anthocyanin over color | medium 5 | |
| Fruit: size | large (383 g) | medium-large 6 |
| Fruit: height | tall 7 (8.5 cm) | |
| Fruit: diameter | large 7 (9.6 cm) | |
| Fruit: ratio height/diameter | large 7 (0.88) | small 3 |
| Fruit: ribbing | absent or weak 1 | absent or weak 1 |
| Fruit: crowning at calyx end | absent or weak 1 | absent or weak 1 |
| Fruit: size of eye | Small 3 | small 3 |
| Fruit: bloom of skin | absent or weak 1 | absent or weak 1 |
| Fruit: greasiness of skin | absent of weak 1 | absent or weak 1 |
| Fruit: surface texture of skin | medium | medium |

-continued

| Characteristics | State for Takano 6 | Aztec (a Fuji Sport) |
|---|---|---|
| Fruit: ground color | 4D (RHS Color Chart) | 4D (RHS Color Chart) |
| Fruit: hue of over color-with bloom removed | red, RHS Orange-Red Group approximately N34A | red |
| Fruit: pattern of over color | solid flush with weakly defined stripes 2 | only solid flush 1 |
| Fruit: width of stripes | medium 5 | |
| Fruit: intensity of over color | weak 3 | medium-dark 6 |
| Fruit: area of russet around stalk attachment | medium 2 | absent or small 1 |
| Fruit: area of russet on cheeks | absent or weak 1 | absent or weak 1 |
| Fruit: area of russet around eye basin | absent or small 1 | absent or small 1 |
| Fruit: number of lenticels | medium 5 | medium 5 |
| Fruit: size of lenticels | small 1 | large 7 |
| Fruit: scarfskin | absent 1 | absent 1 |
| Fruit: length of stalk | medium 5 (2.1 cm) | medium-long 6 |
| Fruit: thickness of stalk | medium 5 (1.9 mm) | medium 5 |
| Fruit: depth of stalk cavity | deep 7 (1.9 cm) | deep 7 |
| Fruit: width of stalk cavity | medium 5 (4.4 cm) | medium 5 |
| Fruit: depth of eye basin | medium 5 (1.1 cm) | deep 7 |
| Fruit: width of eye basin | medium 5 (3.6 cm) | medium 5 |
| Fruit: firmness of flesh | firm 7 (14.5 lbs) | medium 5 |
| Fruit: color of flesh | cream 2 | yellowish 3 |
| Fruit: sweetness of flesh | high (16.0%) Brix | high (16.0%) Brix |
| Fruit: acidity of flesh | medium (0.41 g/100 ml) titratable acidity | low (0.35 g/100 ml) |
| Fruit: water-core of flesh | absent-very slight | |
| Fruit: shape of core | globose 6 | globose 6 |
| Fruit: aperture of locules (in transverse section) | moderately open 2 | moderately open 2 |

I claim:

1. A new and distinct variety of apple tree as illustrated and described herein.

* * * * *